United States Patent
LaRose

(10) Patent No.: US 10,576,191 B2
(45) Date of Patent: Mar. 3, 2020

(54) INFLOW CANNULA

(71) Applicant: HeartWare, Inc., Miami Lakes, FL (US)

(72) Inventor: Jeffrey A. LaRose, Raleigh, NC (US)

(73) Assignee: HeartWare, Inc., Miami Lakes, FL (US)

( * ) Notice: Subject to any disclaimer, the term of this patent is extended or adjusted under 35 U.S.C. 154(b) by 85 days.

(21) Appl. No.: 15/788,345

(22) Filed: Oct. 19, 2017

(65) Prior Publication Data
US 2018/0110908 A1    Apr. 26, 2018

Related U.S. Application Data
(60) Provisional application No. 62/410,513, filed on Oct. 20, 2016.

(51) Int. Cl.
*A61M 1/10* (2006.01)
*A61M 1/12* (2006.01)

(52) U.S. Cl.
CPC .......... *A61M 1/1008* (2014.02); *A61M 1/122* (2014.02); *A61M 1/125* (2014.02)

(58) Field of Classification Search
CPC ..... A61M 1/1008; A61M 1/122; A61M 1/125
See application file for complete search history.

(56) References Cited

U.S. PATENT DOCUMENTS

| | | |
|---|---|---|
| 7,022,100 B1 | 4/2006 | Aboul-Hosn et al. |
| 7,955,298 B2 | 6/2011 | Carroll et al. |
| 9,050,418 B2 | 6/2015 | Schima et al. |
| 2002/0082467 A1 | 6/2002 | Campbell |
| 2013/0303831 A1* | 11/2013 | Evans ............... A61M 1/101 600/16 |
| 2015/0290370 A1 | 10/2015 | Crunkleton et al. |

FOREIGN PATENT DOCUMENTS

WO    2012025199 A1    3/2012

OTHER PUBLICATIONS

International Search Report and Written Opinion dated Mar. 21, 2018 for corresponding International Application No. PCT/US2017/057323; International Filing Date: Oct. 19, 2017 consisting of 13 pages.

* cited by examiner

*Primary Examiner* — George Manuel
(74) *Attorney, Agent, or Firm* — Christopher & Weisberg, P.A.

(57) ABSTRACT

An implantable blood pump including an inflow cannula, the inflow cannula having a malleable tube including an inflow portion, a steering assembly coupled to the inflow portion of the tube, an actuator coupled to the steering assembly for applying a force to the tube, and a cannula tip extending from the inflow portion of the tube and defining an aperture in fluid communication with the tube.

20 Claims, 7 Drawing Sheets

INFLOW CANNULA

CROSS-REFERENCE TO RELATED APPLICATION

This application claims priority to U.S. Provisional Patent Application Ser. No. 62/410,513, filed Oct. 20, 2016, entitled INFLOW CANNULA, the entirety of which is incorporated herein by reference.

STATEMENT REGARDING FEDERALLY SPONSORED RESEARCH OR DEVELOPMENT n/a

TECHNICAL FIELD

The present invention relates to inflow cannulas, and more particularly, to a steerable inflow cannula.

BACKGROUND

Inflow cannulas are used with implantable blood pumps, such as ventricular assist devices ("VAD"), which provide left and/or right heart support. Inflow cannulas typically include a relatively small diameter for positioning of the inflow cannula within a heart chamber using a transvascular or intravascular implantation method. In addition, a number of inflow cannulas include a tapered tip for navigating through the vasculature while attempting to reduce the risk of occluding an opening of the tip susceptible to obstruction from body tissue. Unfortunately, the relatively small diameter and the tapered tip may negatively impact flow capabilities during substantial or complete drainage of the heart chamber. As a further drawback, complete removal of the tip may generate suction through the cannula, thereby increasing the risk of occlusion.

Similar to the implantation of the inflow cannulas, known catheters may be implanted using the transvascular or intravascular approach. For example, steerable catheters include movable tip portions which provide steering through the body using one or more wires anchored on opposing ends of the catheter or in a handle unit. A lever or knob may be actuated to apply or reduce tension on the wires to provide the steering or deflection control. However, such steering catheters include closed tips that do not provide inflow through the catheter.

SUMMARY

The present invention advantageously provides an implantable blood pump including an inflow cannula, the inflow cannula having a malleable tube including an inflow portion, a steering assembly coupled to the inflow portion of the tube, an actuator coupled to the steering assembly for applying a force to the tube, and a cannula tip extending from the inflow portion of the tube and defining an aperture in fluid communication with the tube.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
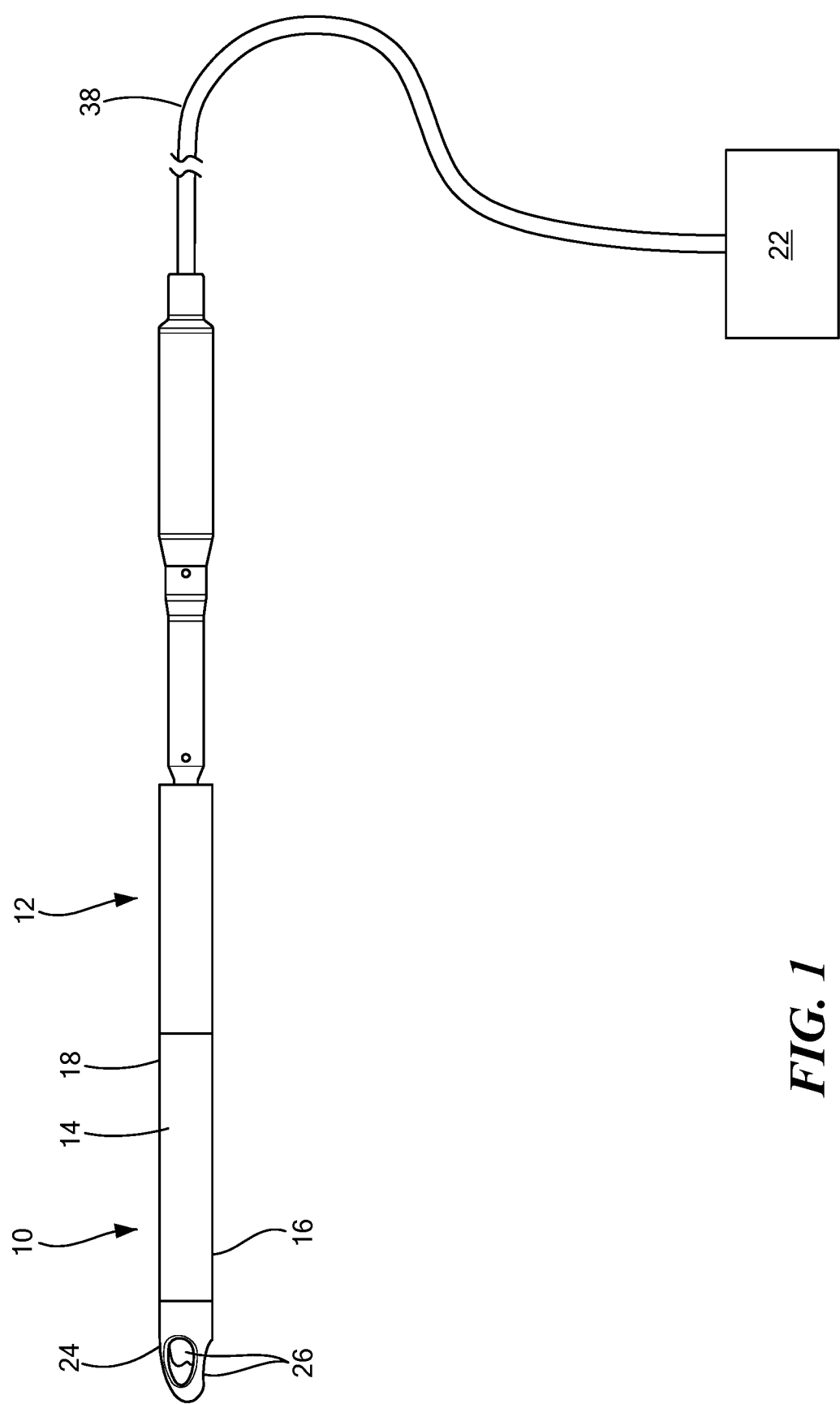
FIG. 1 is a side view of an implantable blood pump including an inflow cannula having a cannula tip.

Before describing in detail exemplary embodiments, it is noted that the embodiments reside primarily in combinations of device and system components related to an inflow cannula. Accordingly, the device and system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawings in which like reference designators refer to like elements, there is shown in FIGS. 1-9 an exemplary inflow cannula constructed in accordance with the principles of the present application and designated generally as "10." The inflow cannula 10 may be an integral part of an implantable blood pump 12 or may be removably coupled to the blood pump 12. The inflow cannula 10 is configured to be maneuvered through a patient's vascular system, or another portion of a patient's body and is configured to allow for a flow rate through the inflow cannula 10 without collapse. In one configuration, the blood pump 12 may be positioned within an aorta and may extend from a left ventricle through an aortic valve into the aorta. The blood pump 12 may be of various types, including but not limited to, a ventricular assist device.

Figure 2:
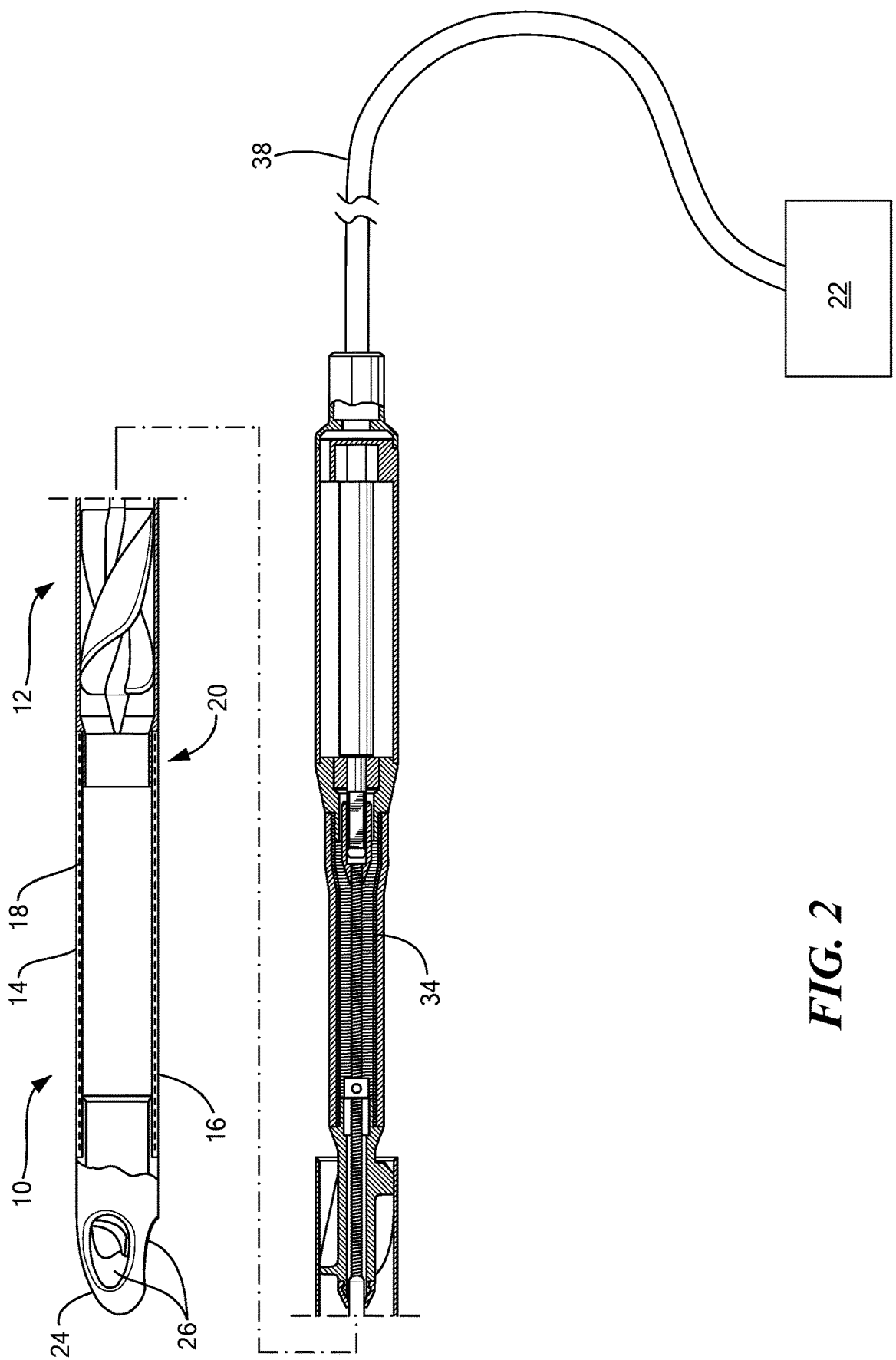
FIG. 2 is a cross-sectional, side view of the implantable blood pump of FIG. 1.

With reference to FIGS. 1 and 2, the inflow cannula 10 may include a tube 14 having a distal portion 16 and a proximal portion 18 opposite the distal portion 16. The distal portion 16 may also be referred to as the inflow portion. The proximal portion 18 of the tube 14 may be coupled to the blood pump 12 in configurations in which the tube 14 is not integral with the blood pump 12. The connection between the inflow cannula 10 and the blood pump 12 may be through any conventional means, including, but not limited to, welding, soldering, etc.

In one configuration, the tube 14 may be made of a malleable material in order to adapt to various positions during implantation and once positioned within the patient's body. For example, the tube 14 may be configured to exhibit sufficient axial compression strength to sustain the forces produced by the inflow cannula 10 when sucking in a fluid, such as the blood. The tube 14 may also be flexible and/or malleable in order to deflect around curves in the patient's vasculature or other portions of the patient's body.

Referring now to FIG. 2, the inflow cannula 10 may include a steering assembly 20 coupled to the inflow portion 16 of the tube 14 to maneuver the tube 14 through the patient's body. The steering assembly 20 may be that which is known in the art, such as the steering assemblies used with steering catheters, as disclosed in U.S. Pat. No. 7,955,298, which is commonly owned and incorporated by reference herein. For example, the steering assembly 20 may be a pull-wire steering assembly or another steering assembly configured to steer, guide, or deflect portions of the inflow cannula 10 in various directions.

In one configuration, an actuator 22 may be coupled to the steering assembly 20 for maneuvering the inflow cannula 10 from an external location. In addition, a cannula tip 24 may extend from the inflow portion 16 of the tube 14. The actuator 22 may be configured to apply a force or torque to the tube 14 and/or the tip 24 to cause the tube 14 and/or the tip 24 to bend or deflect. The tip 24 may define an aperture 26 in fluid communication with the tube 14, as explained in further detail herein.

Figure 3:
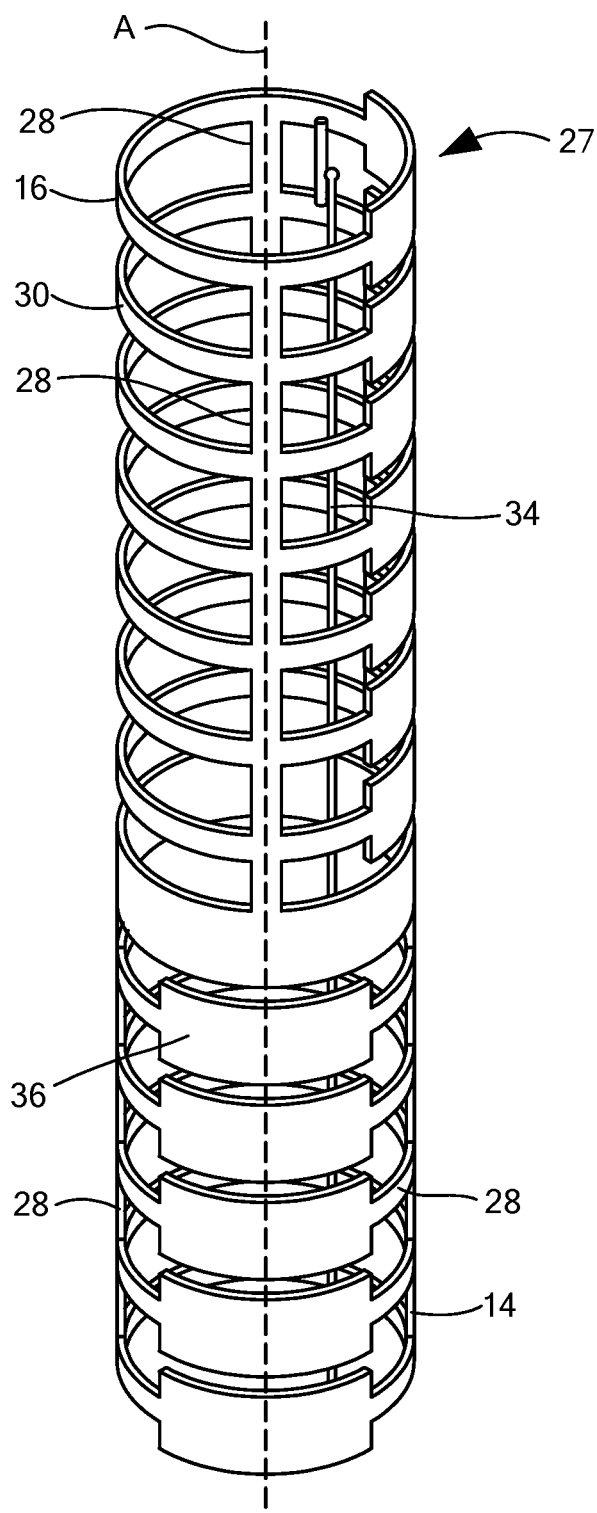
FIG. 3 is a front view of the inflow cannula of FIG. 1 including a steering assembly having a deflection section.

With reference to FIG. 3, the steering assembly 20 of the inflow cannula 10 is shown including a deflection section 27. In one exemplary configuration, the deflection section 27 may include at least two elongated members 28. Various materials may be used to construct the elongated members 28, including, but not limited to NiTi, spring steel, and carbon fiber. The elongated members 28 may be disposed along at least a portion of the tube 14, such as the distal portion 16 and/or the proximal portion 18 of the tube 14. The elongated members 28 may also be an integral part of the tube 14 or may be removably coupled to the tube 14. For example, in one configuration the elongated members 28 may include a first elongated member 30 coupled to the distal portion 16 of the tube 14 and a second elongated member 32 coupled to the proximate portion 18 of the tube 14.

One or more actuator members, such as a pull wire 34, may be disposed within the inflow cannula 10 and coupled to the tube 14. One or more ribs 36 may be disposed along the elongated members 28. The ribs 36 may be circular or another shape which defines a deflection profile of the deflection section 27. Each rib 36 is shown defining a plane perpendicular to a tube axis spanning from the distal portion 16 to the proximal portion 18. In the example shown in FIG. 1, the pull wire 34 may be coupled to the tip 24. In the example shown in FIG. 3, the pull wire 34 may be coupled to the inflow portion 16 of the tube 14. The elongated members 28 may be made of a spring material configured to bend or deflect by applying a force, such as tension, to the pull wire 34. In the alternative, the elongated members 28 may be made of another material, such as a shape-memory material, configured to deflect upon exposure to select temperatures.

Figure 4:
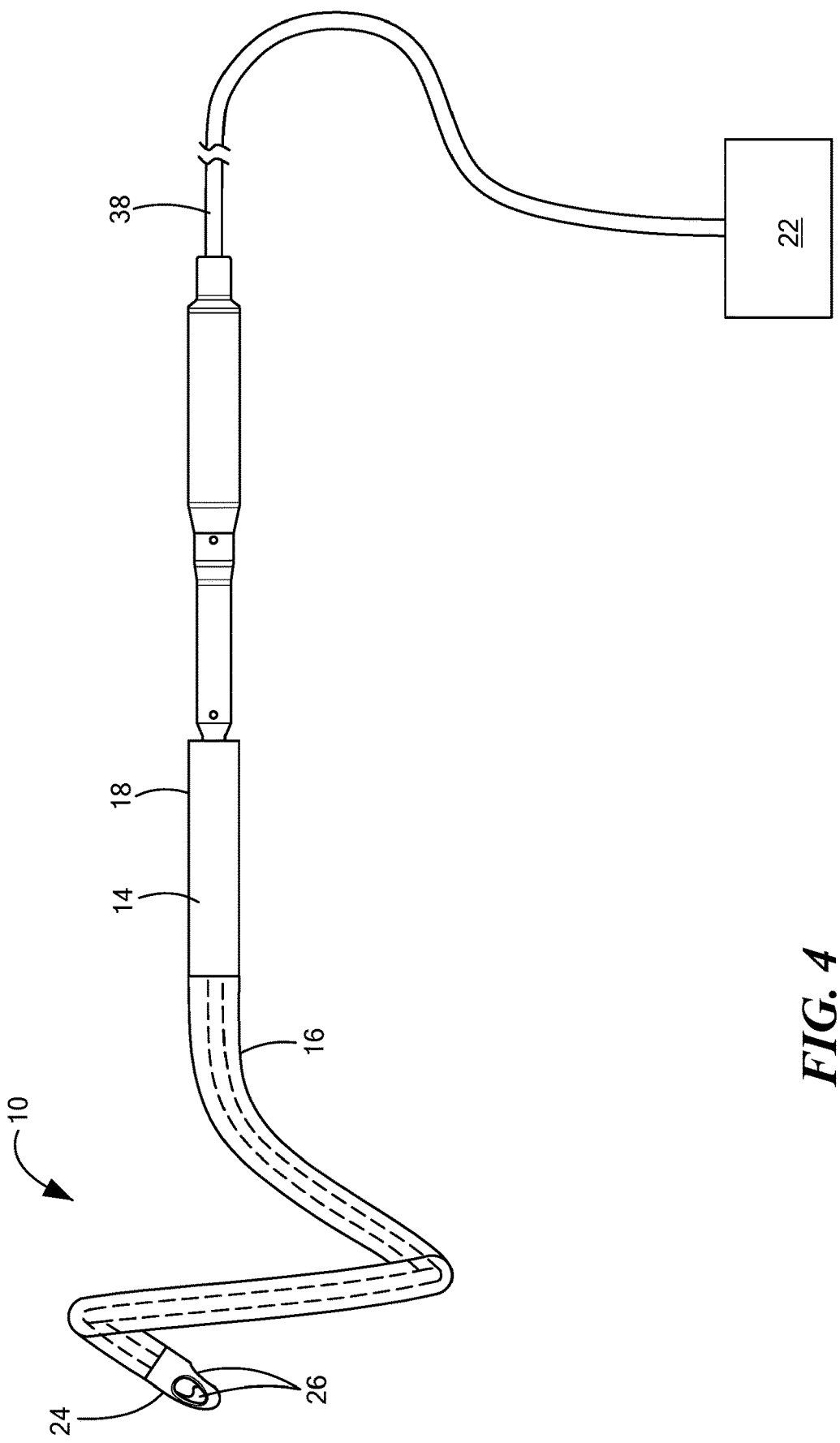
FIG. 4 is a side view of the implantable blood pump of FIG. 1 including the inflow cannula in a deflected configuration.

With reference to FIG. 4, a force may be applied to the pull wire 34 through the actuator 22, causing at least a portion of the tube 14 to bend or deflect to achieve a deflected configuration. The portion of the tube 14 configured to bend or deflect may vary depending upon the location of the pull wire 34 with respect to the elongated members 28 and/or the tip 24. In other words, the portion of the inflow cannula 10 configured to bend or deflect may vary depending upon the structure and material of the tube 14 and the steering assembly 20. The deflection section 27 may take a pre-determined shape that is defined by the physical construction of the individually ribs 36. In one configuration, the pull wire 34 may be pulled in a direction toward the actuator 22 to bend and/or steer the tip 24 when the pull wire 34 is coupled to the tip 24. As such, the tip 24 may be movable with respect to the tube 14. When the tube 14 and/or the tip 24 are in the bent or deflected state, the tube 14 is configured to be steerable through the vasculature or another portion of the patient's body. As shown in FIG. 4, in one configuration, the pull wire 34 may extend through a driveline 38 from inside the patient's body to outside of the patient's body. The driveline 38 may be coupled to the actuator 22, which may be a lever, a knob, a handle, controller, or the like.

Figure 6:
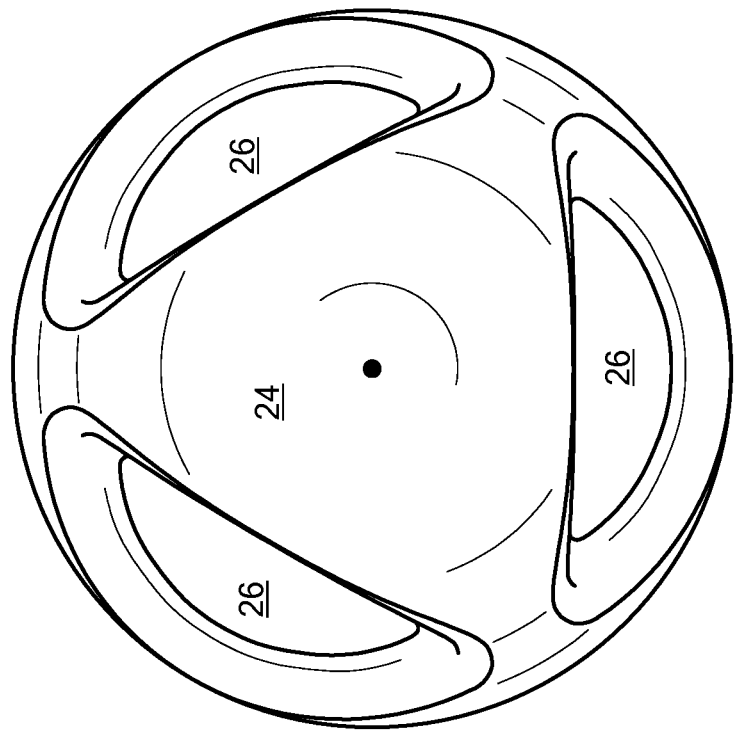
FIG. 6 is a bottom view of the cannula tip of FIG. 5.
Figure 5:
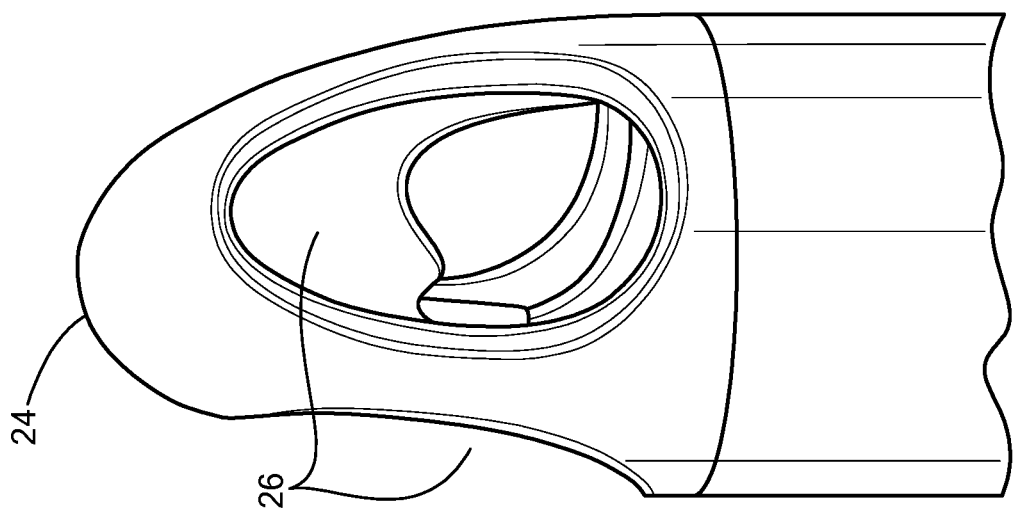
FIG. 5 is a side view of a cannula tip of the inflow cannula of FIG. 1.

With reference to FIGS. 5 and 6, a close-up, side-elevational view, and a bottom view, respectfully, of the tip 24 are shown with the tip 24 including a smooth tapered outer surface defining at least two apertures 26. For example, in one configuration, the tip 24 includes three apertures 26a-26c which allow a fluid, such as blood, to flow through the apertures 26 into the tube 14. In one example, the tip 24 may be that which is described in U.S. Pat. No. 9,050,418, to HeartWare, Inc., which is incorporated by reference herein in the entirety. Similar to the tube 14, the tip 24 may be malleable but is configured to withstand the suction forces produced by the fluid entering the tube 14. The tip 24 may be an integral part of the inflow cannula 10 or may be removably coupled to the tube 14 using conventional methods known in the art, such as adhesive, welding, or the like.

In one configuration, the apertures 26 may be evenly spaced from each other around a circumference of the tip 24 such that, during use, the lateral forces on the tip 24 caused by the suction of the fluid may be neutralized at the tip 24. For example, when the tube 14 is implanted within the heart chamber, the tip 24 may be positioned toward a middle of the heart chamber such that the tip 24 is unexposed to the lateral forces which would cause the tip 24 to migrate toward the heart tissue. As such, the tip 24 is configured to decrease the risk of or prevent occlusion, which may otherwise occur as a result of the tip 24 being in contact with the heart tissue.

In one configuration, the apertures 26 include a circular shape to further minimize the risk of occlusion while allowing a relatively high flow rate through the tip 24. In other configurations, the apertures 26 of the tip 24 may include various spatial arrangements. Similarly, the shape and the number of apertures 26 of the tip 24 may vary in accordance with various design.

Figure 7:
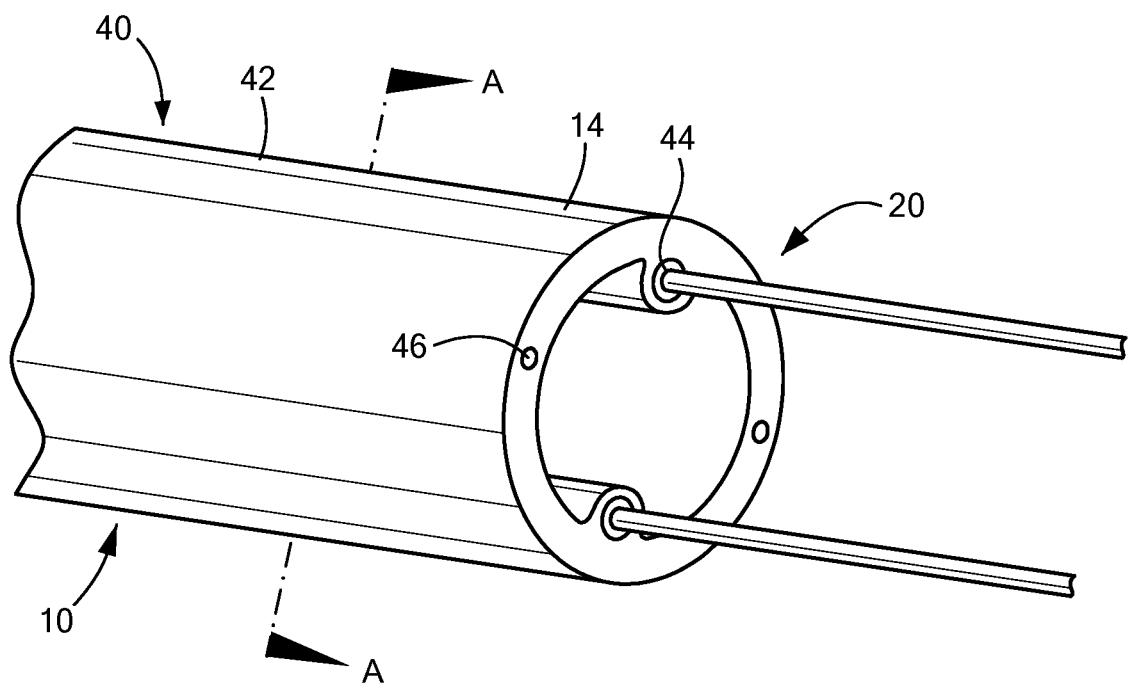
FIG. 7 is a perspective view of a steering assembly of the inflow cannula of FIG. 1.

With reference to FIG. 7, another configuration of a deflection section 40 of the steering assembly 20 is shown including the deflection section 40 defined by a wall 42 which may be manufactured from a malleable or resilient material. One or more actuator members 44 and one or more elongated members 46 may be embedded within or on the wall 42. The actuator members 44 may be pull wires, tape, or another structure configured to receive the force of the actuator 22 (FIG. 4) to cause the bending and/or deflecting. The actuator members 44, the elongated members 46, and the wall 42 define the plane and shape of the bending and/or deflection of the deflection section 40. In addition, the structure of the tube 14 provides for torque transfer between the actuator 22 and the deflection section 40 and thus to the tip 24.

Figure 8:
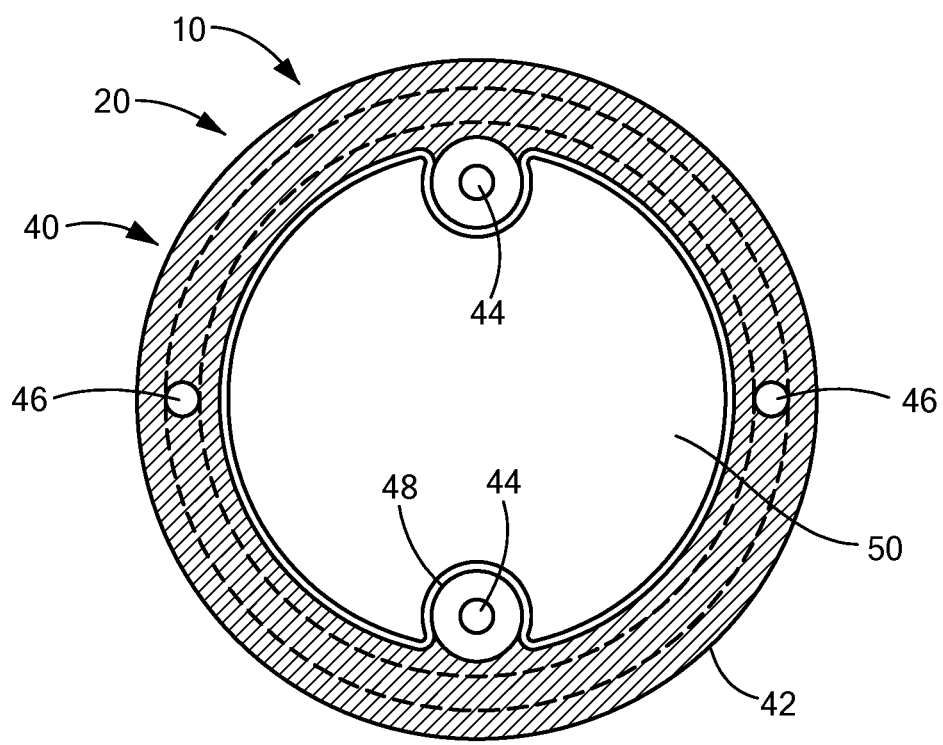
FIG. 8 is a cross-sectional front view of the steering assembly of FIG. 7.

Referring now to FIG. 8, which is a sectional view taken along section A-A in FIG. 7, the elongated members 46 are shown embedded within the wall 42. The elongated members 46 have a fixed rigidity greater than a rigidity of the wall 42. The actuator members 44 may be located within a deflection conduit 48. FIG. 8 shows two elongated members 46 aligned radially 180 degrees from one another within the wall 42 and two deflection conduits 48 radially aligned 180 degrees from one another on the wall 42. The elongated members 46 and/or the deflection conduits 48 may be embedded within the wall 42 during formation of the wall 42 or can be attached to the wall 42 by known methods, such as adhesive. In the alternative, the elongated members 46 may be coupled to a coil within or adjacent the wall 42 (not shown) to define a preferred deflection shape and/or plane. The rigidity of the wall 42 may be adjusted to provide a different radius of bend when the force from the actuator 22 is applied to the deflection section 40. The wall 42 is shown defining a lumen 50 which provides for the passage of the fluid, such as the blood, from the tip 24 through the inflow cannula 10.

Figure 9:
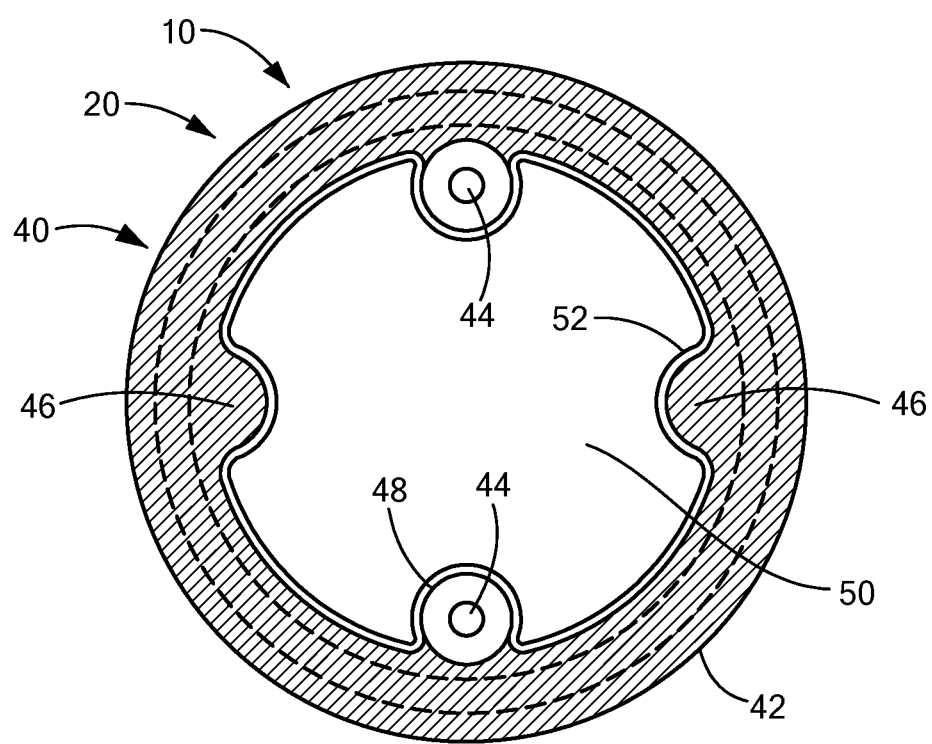
FIG. 9 is a cross-sectional front view of the steering assembly of FIG. 7.

With reference now to FIG. 9, an alternate cross-sectional view of the inflow cannula 10 is shown including a rib 52 protruding into the lumen 50 from the wall 42. The rib 52 extends at least a portion of a length of the deflection section 40. The elongated members 46 may be positioned within rib 52. The rib 52 may be constructed from material that can have a varying rigidity along its length. By controlling the rigidity of the rib during manufacturing, a preferred deflection shape can be defined by controlling bend radii along the length of the rib 52. By providing variable rigidity along the length of rib 52, variable resistance to a bending force is provided, thereby defining one or more bend shapes and planes of deflection. For example, one or more areas of the rib 52 having a greater rigidity will have a greater radius of bend compared to one or more areas of the rib 52 with a lesser rigidity which has a lesser radius of bend per unit force applied by the actuator members 44. As discussed above, one or more deflection conduits 48 and one or more elongated members 46 can be provided at variable locations along the wall 42. Thus, it has advantageously been found that deflection shape and deflection plane alignment can be defined by varying the rigidity of wall 226 or the rib 52, while maintaining a constant rigidity of the elongated members 46.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An implantable blood pump including an inflow cannula, the inflow cannula comprising:
    a malleable tube having an inflow portion, the malleable tube having a constant diameter over its entire length along the major longitudinal axis;
    a steering assembly coupled to the inflow portion of the tube;
    an actuator coupled to the steering assembly for applying a force to the tube; and
    a cannula tip extending from the inflow portion of the tube and defining an aperture in fluid communication with the tube.

2. The inflow cannula according to claim 1, further comprising an actuator member coupled to the cannula tip.

3. The inflow cannula according to claim 2, wherein the actuator member is a pull wire disposed within at least a portion of the inflow cannula.

4. The inflow cannula according to claim 1, wherein the steering assembly includes a pull wire, and the inflow cannula includes a driveline having the pull wire extending therethrough.

5. The inflow cannula according to claim 1, wherein the steering assembly includes a deflection section including a plurality of elongated members and a plurality of ribs extending along the plurality of elongated members.

6. The inflow cannula according to claim 1, wherein the steering assembly includes at least one rib disposed within the tube.

7. The inflow cannula according to claim 1, wherein the steering assembly includes a plurality of elongated members embedded within the tube and an actuator member coupled to at least one of the plurality of elongated members.

8. The inflow cannula according to claim 1, wherein the cannula tip defines three apertures evenly spaced from each other around a circumference of the cannula tip.

9. The inflow cannula according to claim 8, wherein the cannula tip includes a smooth tapered outer surface.

10. An inflow cannula for use with an implantable blood pump comprising:
    a tube of constant diameter over its entire length along the major longitudinal axis having a proximal portion and a distal portion opposite the proximal portion, the distal portion having a tip extending therefrom, the tip defining an aperture in fluid communication with the tube;
    a steering assembly coupled to the tip; and
    an actuator coupled to the steering assembly for applying a force to the tip.

11. The inflow cannula according to claim 10, wherein at least one of a group consisting of the tube and the tip are made of a malleable material.

12. The inflow cannula according to claim 11, wherein the tip is moveable with respect to the tube.

13. The inflow cannula according to claim 10, wherein the tip includes a tapered outer surface defining a plurality of apertures in fluid communication with the tube.

14. The inflow cannula according to claim 10, wherein the proximal portion of the tube is coupled to the implantable blood pump.

15. The inflow cannula according to claim 10, wherein the steering assembly includes a pull wire, and the inflow cannula includes a driveline having the pull wire extending therethrough.

16. The inflow cannula according to claim 10, further comprising a deflection section including a plurality of elongated members embedded within the tube and a plurality of actuating members coupled to the tube.

17. The inflow cannula according to claim 10, wherein the steering assembly includes a first elongated member coupled to the distal portion of the tube and a second elongated member coupled to the proximal portion of the tube.

18. The inflow cannula according to claim 10, further comprising a pull wire coupled to the tip.

19. The inflow cannula according to claim 10, wherein the actuator is at least one of a group consisting of a lever, a knob, and a handle.

20. An inflow cannula for use with an implantable blood pump comprising:
- a tube of constant diameter over its entire length along the major longitudinal axis having a proximal portion and a distal portion opposite the proximal portion, the distal portion having a tip extending therefrom, the tip defining an aperture in fluid communication with the tube, and the proximal portion being coupled to the implantable blood pump;
- a steering assembly coupled to the tip, the steering assembly including a plurality of elongated members and an actuator member coupled to at least one of the plurality of elongated members; and
- an actuator coupled to the steering assembly for applying a force to the tip.

\* \* \* \* \*